United States Patent [19]

Schluenz et al.

[11] 4,055,576

[45] Oct. 25, 1977

[54] PROCESS FOR THE PREPARATION OF TERPENE-MALEIC ANHYDRIDES CONTAINING LESS THAN 15% DI-ADDUCT

[75] Inventors: Robert William Schluenz; Curry Beach Davis, both of Panama City, Fla.

[73] Assignee: Arizona Chemical Company, Wayne, N.J.

[21] Appl. No.: 678,083

[22] Filed: Apr. 19, 1976

[51] Int. Cl.$^2$ ............................................. C07D 307/89
[52] U.S. Cl. ............................... 260/346.6; 260/346.3; 260/346.76; 260/346.74
[58] Field of Search .................... 260/346.8 R, 346.6, 260/346.3

[56] References Cited

U.S. PATENT DOCUMENTS

| | | | |
|---|---|---|---|
| 1,993,031 | 3/1935 | Peterson | 260/346.6 |
| 2,208,321 | 7/1940 | Bradley | 260/346.6 |
| 2,839,550 | 6/1958 | Wiggerink et al. | 260/346.8 R |

OTHER PUBLICATIONS

Egger et al., J. Am. Chem. Soc. vol. 88, pp. 241–246 (1966).

*Primary Examiner*—Henry R. Jiles
*Assistant Examiner*—Bernard Dentz
*Attorney, Agent, or Firm*—Harry H. Kline

[57] ABSTRACT

There is provided a process for preparing the reaction product of maleic anhydride with a non-conjugated mono-cyclic terpene in the presence of controlled amounts of iodine to attain a mixture of not more than 15% di-adducts and the balance of said mixture being mono-adducts.

7 Claims, No Drawings

PROCESS FOR THE PREPARATION OF TERPENE-MALEIC ANHYDRIDES CONTAINING LESS THAN 15% DI-ADDUCT

The present invention relates to a process for preparing maleic anhydride adducts of non-conjugated terpenes. More particularly, it relates to a process for preparing the reaction product of maleic anhydride with a non-conjugated monocyclic terpene. Still more particularly, the invention is concerned with a process for preparing at elevated temperatures the reaction product of maleic anhydride with a non-conjugated, monocyclic terpene in the presence of controlled amounts of iodine to attain a mixture of not more than 15% di-adducts and the balance of said mixture being mono-adducts in good color, yield and purity.

It is known that maleic anhydride and terpenes, both conjugated and unconjugated, can form maleic anhydride adducts under elevated temperatures. However, the yields of resultant adduct, particularly mono-adduct, are unsatisfactory. It is also known that, if small amounts of mineral acid are present during adduct formation, non-conjugated terpenes can be used. Nonetheless, resultant yield of mono-adduct is unsatisfactory and generally dark in color. If a process could be provided whereby good yields of mono-adduct, in pale color while employing maleic anhydride and non-conjugated terpenes can be prepared, such would fulfill, a long felt need in the art.

It is, therefore, a principal object of the invention to provide a process for preparing in good yields mono-adducts from non-conjugated monocyclic terpenes and maleic anhydride. It is a further object of the invention to prepare mono-adducts in yields of at least 85% from non-conjugated terpenes and maleic anhydride. Other objects and advantages will become apparent from a reading of the following description.

According to the process of the present invention, a mixture containing not less than 85% mono-adducts and not more than 15% di-adducts is obtained by reacting a non-conjugated monocyclic terpene with maleic anhydride at elevated temperatures in the presence of iodine. The adduct mixture so obtained finds utility as a reactive medium in the presence of a polyamine to form resinous terpene-maleimides useful as tackifiers for polar elastomers, as a liquid curing agent for epoxy resins, and in the manufacture of alkyd resins.

In general, equimolar amounts of a suitable non-conjugated terpene and maleic acid anhydride are reacted at temperatures ranging from about 175° C. to 200° C. in the presence of from 0.05% to 0.15% iodine, and preferably between 0.08% and 0.12%, based on the weight of the terpene. It has been found, however, that an excess of either the maleic anhydride or terpene can be employed without materially affecting the overall yields of the respective adducts obtained.

Illustrative of the non-conjugated monocyclic terpenes or dienes which can be employed herein are: limonene, terpinolene, terpineol, 1,4-para methadiene and cineoles, such as 1,8-cineole, 1,4-cineole, or mixtures of the same.

In order to facilitate a further understanding of the invention, the following examples are presented primarily for the purpose of illustrating more specific details thereof. The invention is not to be deemed limited thereby except as defined in the claims. Unless otherwise noted, all parts are by weight.

EXAMPLE 1

To a suitable flask equipped with an overhead stirrer, additional funnel, thermometer, inlet for nitrogen, and a condenser above a water trap filled with toluene which is placed above a short, packed column, are added 588 parts of maleic anhydride and 30 parts (by volume) of toluene. The mixture is heated to 200° C. for about 30 minutes. During this time, the system is dried by the refluxing toluene-water azeotrope. The temperature is reduced to 170°–180° C., or below reflux, and 1.1 parts (0.12%, based on the weight of the terpene to be added) of iodine are introduced. Next, 906 parts of a terpene fraction containing about 90% terpinolene, the remainder being terpene hydrocarbons and mono-unsaturated, monocyclic terpene alcohols are added while maintaining the temperature at about 180° C. The temperature is next raised to 190°–195° C. after addition of the latter terpene fraction. Reflux is maintained by periodic addition of toluene. Thereafter, the temperature is further raised to 200° C. and held for 2 hours. The reaction mixture is cooled to 100° C. A distillation head is attached and vacuum then applied. The temperature is next raised to 160° C. and steam is introduced for a 15 minute stripping period at a temperature of about 200° C. whereby volatiles are removed.

There is recovered a yield of 1360 parts of a maleic anhydride terpene adduct mixture comprising 95% mono-adduct and about 5% di-adduct. The latter percentages are determined by gel permeation chromatography (GPC). The resultant mixture, obtained in 91% yields is a pale yellow liquid at ambient temperatures, having the following properties:

| | |
|---|---|
| Color (Gardner) | 4 |
| Equivalent Weight | 120 |
| Viscosity (Gardner-Holdt, 25° C) | Z-3 |
| Unsaponifiables, % | 2.4 |
| Specific Gravity, 25°/25° C | 1.134 |
| Ash, % | 0.01 |

EXAMPLE 2

Repeating the procedure of Example 1 in every detail except that no iodine is incorporated during the reaction.

There is obtained a product weighing 1135 parts which is equivalent to a 76% yield. This product is characterized by GPC analysis as containing about 55% mono-adduct and about 45% of di-adduct. The resultant product is a dark yellow solid.

EXAMPLE 3

The process of Example 1 is repeated in every detail except that the terpene fraction therein is substituted by 930 parts of a terpene fraction comprising about 40% terpinolene, 25% dipentene, 30% cineoles, and the balance being terpene hydrocarbons and mono-unsaturated, monocyclic terpene alcohols.

Resultant adduct mixture which is recovered in a yield of about 90%, is substantially the same as that obtained in Example 1.

EXAMPLE 4

Repeating the procedure of Example 1 in every detail except that 97% llimonene is substituted for the terpene fraction therein. There is obtained a terpene maleic anhydride adduct in a yield of about 92% having more than 95% of the mono-adduct in said mixture, said mixture being a pale yellow liquid.

EXAMPLE 5

This example illustrates the continuous procedure for preparing the adduct mixture of the present invention.

Liquid maleic acid anhydride maintained at 100° C. and the liquid terpene fraction of Example 1 above maintained at 20° C. to 25° C. and xylene are introduced in a suitable reactor as defined in Example 1 above, in a ratio of 6.2/9.6/6.2, respectively. Prior to introduction, each reactant is passed through a heat exchanger, the temperature is raised to 120° C. and then discharged into a jacketted kettle with a reflux container containing a small initial charge of xylene. Iodine is separately fed into the kettle at a rate equal to 0.12 part per 100 parts of terpene. The contents of the kettle are stirred and the mixture is maintained at 200° C. by the dissipation of heat in the condenser and jacketted kettle. Any water formed is removed as an azeotrope from the reflux stream.

The product mixture overflows into a second reactor after a 2 hour residence time. The temperature in the second reactor is maintained at 200° C. for 1 hour and the product an overflow is vacuum steam stripped to yield the desired mono-adduct. Charging of 6250 parts of maleic anhydride and 9600 parts of the terpinolene fraction results in a 90% yield of the adduct mixture which is a pale yellow liquid at 25° C. containing a mono to di-adduct ratio of 90/10, respectively.

Resultant product is stored as such or is converted directly to a terpene imide resin which finds utility as a component in elastomer formulations for use in adhesive hot melts.

EXAMPLE 6

This example illustrates terpene-maleimide preparation.

The product of Example 5 is reacted under reflux temperatures with a stoichiometric amount of ethylene diamine which is added slowly, while stirring, to the mixture. Any formed water is removed as an azeotrope from the reflux stream. When the addition of the diamine is complete, the kettle temperature is raised to 240° C. by stripping off xylene and water is continuously removed as an azeotrope. After reaching 240° C. kettle temperature, the mixture is vacuum steam stripped 3 hours to remove volatile oils. The stripped resin is then cooled and drumed or flaked and bagged.

Resultant yellow solid product whose softening point is 91° C. has a number of average molecular weight equal to 520.

EXAMPLE 7

Substituting an equimolar amount of trimethylene diamine for ethylene diamine in Example 6 above, there is obtained a yellow solid resinous terpene-maleimide having an average molecular weight equal to about and a softening point equal to 75° C.

We claim:

1. A process for preparing maleic anhydride adducts from non-conjugated monocyclic terpenes which comprises: reacting at temperatures between 175° C. and 200° C. substantially equimolar amounts of (a) a non-conjugated monocyclic terpene or mixed non-conjugated monocyclic terpenes and (b) maleic acid anhydride in the presence of from 0.05% to 0.15% iodine, based on the weight of the terpene, and recovering a mixture of not less than 85% mono-adduct and not more than 15% di-adduct of terpene maleic adduct in good yield, color and purity.

2. The process according to claim 1 wherein the terpene is principally terpinolene.

3. The process according to claim 1 wherein the terpene mixture comprises principally terpinolene and cineole.

4. The process according to claim 1 wherein the terpene is limonene.

5. The process according to claim 1 wherein the iodine added is 0.12%, based on the weight of the terpene reactant.

6. The process according to claim 1 wherein the temperature employed is 200° C.

7. The process according to claim 1 wherein the process is conducted continuously.

* * * * *